(12) United States Patent
Miura et al.

(10) Patent No.: US 8,105,630 B2
(45) Date of Patent: Jan. 31, 2012

(54) COMPOSITION CONTAINING MEDICINE EXTREMELY SLIGHTLY SOLUBLE IN WATER BEING EXCELLENT IN ELUTING PROPERTY AND METHOD FOR PREPARATION THEREOF

(75) Inventors: Hiroshi Miura, Fuji (JP); Makoto Kanebako, Sunto-gun (JP); Masayuki Kanishi, Numadu (JP); Toshio Inagi, Mishima (JP); Hirofumi Takeuchi, Gifu (JP); Tsutomu Kajino, Toyoake (JP); Yoshiaki Fukushima, Aichi-gun (JP); Haruo Takahashi, Ohgaki (JP)

(73) Assignees: Kowa Co., Ltd., Nagoya-shi (JP); Kabushiki Kaisha Toyota Chuo Kenkyusho, Aichi-gun (JP)

( * ) Notice: Subject to any disclaimer, the term of this patent is extended or adjusted under 35 U.S.C. 154(b) by 595 days.

(21) Appl. No.: 10/554,921

(22) PCT Filed: Apr. 28, 2004

(86) PCT No.: PCT/JP2004/006139
§ 371 (c)(1),
(2), (4) Date: Oct. 31, 2005

(87) PCT Pub. No.: WO2004/096281
PCT Pub. Date: Nov. 11, 2004

(65) Prior Publication Data
US 2006/0293327 A1    Dec. 28, 2006

Related U.S. Application Data

(60) Provisional application No. 60/466,051, filed on Apr. 29, 2003.

(51) Int. Cl.
*A61K 31/50* (2006.01)
*A61K 9/00* (2006.01)

(52) U.S. Cl. ......... 424/489; 424/400; 514/247; 977/906

(58) Field of Classification Search .................. 424/489; 514/247, 252; 426/239; 521/33
See application file for complete search history.

(56) References Cited

U.S. PATENT DOCUMENTS

| | | | |
|---|---|---|---|
| 6,348,468 B1 * | 2/2002 | Ohkuchi et al. | 514/252.03 |
| 6,753,330 B2 * | 6/2004 | Takano et al. | 514/247 |
| 2002/0047058 A1 * | 4/2002 | Verhoff et al. | 241/26 |
| 2004/0058956 A1 * | 3/2004 | Akiyama et al. | 514/318 |

FOREIGN PATENT DOCUMENTS

| | | | |
|---|---|---|---|
| JP | 61-227520 | | 10/1986 |
| JP | 6-040714 | | 2/1994 |
| JP | 2000-53668 | | 2/2000 |
| JP | 2000-198776 | | 7/2000 |
| JP | 2002-345940 | * | 3/2002 |
| JP | 2002-302435 | | 10/2002 |
| JP | 2002-345940 | * | 12/2002 |
| WO | 02/20624 | | 3/2002 |
| WO | WO 02/20624 | * | 3/2002 |
| WO | 02/051381 | | 7/2002 |
| WO | 02/060411 | | 8/2002 |

OTHER PUBLICATIONS

Website: www.sigma-aldrich.com (silica gel product 403563).*
Fuji Silysia MSDS downloaded May 31, 2010 in pdf format (properties of silica material); 6 pp.*
U.S. Appl. No. 11/813,968, filed Jul. 13, 2007, Miura, et al.
David D. Hile, et al., "Active growth factor delivery from poly(D,L-lactide-co-glycolide) foams prepared in supercritical CO2", Journal of Controlled Release, vol. 66, pp. 177-185 2000.
Petra Sencar-Bozic, et al, "Improvement of nifedipine dissolution characteristics using supercritical CO2", International Journal of Pharmaceutics, vol. 148, pp. 123-130 1997.
U.S. Appl. No. 10/551,901, filed Oct. 4, 2005, Miura, et al.

* cited by examiner

*Primary Examiner* — Robert A Wax
*Assistant Examiner* — Jeffrey T Palenik
(74) *Attorney, Agent, or Firm* — Oblon, Spivak, McClelland, Maier & Neustadt, L.L.P.

(57) ABSTRACT

A composition containing an extremely poorly water-soluble drug and obtained by treating, with a supercritical fluid or subcritical fluid of carbon dioxide, a mixture comprising a porous silica material and the extremely poorly water-soluble drug; and its production process. The porous silica material has an average pore diameter in a range of from 1 to 20 nm, pores having diameters within ±40% of the average pore size account for at least 60% of a total pore volume of the porous silica material, and in X-ray diffractometry, the porous silica material has at least one peak at a position of diffraction angle (2θ) corresponding to a d value of at least 1 nm.

The composition according to the present invention, which contains the extremely poorly water-soluble drug, is excellent in the dissolution of the extremely poorly water-soluble drug.

15 Claims, No Drawings

COMPOSITION CONTAINING MEDICINE EXTREMELY SLIGHTLY SOLUBLE IN WATER BEING EXCELLENT IN ELUTING PROPERTY AND METHOD FOR PREPARATION THEREOF

TECHNICAL FIELD

This invention relates to compositions containing an extremely poorly water-soluble drug and permitting excellent dissolution, and also to a production process thereof.

BACKGROUND ART

2-Benzyl-5-(4-chlorophenyl)-6-[4-(methylthio)phenyl]-2H-pyridazin-3-one is known to have excellent interleukin-1β production inhibiting effect and to be useful as preventives and therapeutics for immune system diseases, inflammatory diseases, ischemic diseases and the like (JP-A-12-198776). However, this compound is a drug having extremely low solubility in water and is poor in its dissolution from preparations. There is, accordingly, an outstanding demand for an improvement in its dissolution.

As methods for improving the dissolution of extremely poorly water-soluble drugs, techniques such as the micronization of the drugs and the preparation of derivatives of the drugs are known. Concerning extremely poorly water-soluble drugs such as 2-benzyl-5-(4-chlorophenyl)-6-[4-(methylthio)phenyl]-2H-pyridazin-3-one, however, micronization cannot improve their dissolution, and their conversion into derivatives leads to changes in drug activities and therefore, is not preferred.

Also proposed as methods for making improvements in dissolution include a method which comprises treating a physiologically active substance such as nifedipine with carbon dioxide, which is in a supercritical state or subcritical state, or with liquid carbon dioxide (for example, JP-A-2002-302435). These methods can improve the dissolution of slightly water-soluble drugs such as nifedipine, but cannot improve the dissolution of extremely poorly water-soluble drugs such as 2-benzyl-5-(4-chlorophenyl)-6-[4-(methylthio)phenyl]-2H-pyridazin-3-one.

DISCLOSURE OF THE INVENTION

An object of the present invention is, therefore, to provide a composition containing an extremely poorly water-soluble drug and permitting excellent dissolution and also its production process.

With the foregoing in view, the present inventors have proceeded with an extensive investigation. As a result, it has been found that a composition excellent in the dissolution of a extremely poorly water-soluble drug can be obtained when a mixture comprising a porous silica material and the extremely poorly water-soluble drug is treated with a supercritical fluid or subcritical fluid of carbon dioxide, provided that the porous silica material has an average pore diameter in a range of from 1 to 20 nm, pores having diameters within ±40% of the average pore size account for at least 60% of a total pore volume of the porous silica material, and in X-ray diffractometry, the porous silica material has at least one peak at a position of diffraction angle (2θ) corresponding to a d value of at least 1 nm. The above finding has led to the completion of the present invention.

Described specifically, the present invention provides a composition containing an extremely poorly water-soluble drug and obtained by treating, with a supercritical fluid or subcritical fluid of carbon dioxide, a mixture comprising a porous silica material and the extremely poorly water-soluble drug, characterized in that the porous silica material has an average pore diameter in a range of from 1 to 20 nm, pores having diameters within ±40% of the average pore size account for at least 60% of a total pore volume of the porous silica material, and in X-ray diffractometry, the porous silica material has at least one peak at a position of diffraction angle (2θ) corresponding to a d value of at least 1 nm; and also a process for the production of the composition.

By the present invention, a composition, which contains an extremely poorly water-soluble drug and permits excellent dissolution, and its production process can be provided.

BEST MODES FOR CARRYING OUT THE INVENTION

The extremely poorly water-soluble drug for use in the present invention can have a solubility of lower than 10 µg/mL, preferably lower than 5 µg/mL, particularly preferably not higher than 1 µg/mL in water at 25° C.

No particular limitation is imposed on the kind of the extremely poorly water-soluble drug for use in the present invention. Examples include antipyretics, anti-inflammatories, analgesics, ataractics, sedatives, antitumor agents, antimicrobials, antibiotics, antilipemics, antitussives/expectorants, muscle relaxants, antiepileptics, antiulcers, antidepressants, antiallergics, cardiotonics, antiarrhythmics, vasodilators, hypotensors/diuretics, diabetes therapeutics, tuberculostatics, antirheumatics, steroids, narcotic antagonists, hormones, fat-soluble vitamins, anticoagulants, ischemic disease therapeutics, immune disease therapeutics, Alzheimer's disease therapeutics, osteoporosis therapeutics, angiopoiesis therapeutics, retinosis therapeutics, retinal vein occlusion therapeutics, senile disciform macular degeneration, cerebrovascular spasm therapeutics, cerebral thrombosis therapeutics, cerebral infarction therapeutics, cerebral occlusion therapeutics, intracerebral hemorrhage therapeutics, subarachnoid hemorrhage therapeutics, hypertensive encephalopathy therapeutics, transient cerebral ischemic attack therapeutics, multi-infarct dementia therapeutics, arterial sclerosis therapeutics, Huntington's disease therapeutics, brain tissue disorder therapeutics, optic neuropathy therapeutics, glaucoma therapeutics, ocular hypertension therapeutics, retinal detachment therapeutics, arthritis therapeutics, antisepsis drugs, antiseptic shock drugs, antiasthma drugs, pollakiuria/incontinentia therapeutics, atopic rhinitis therapeutics, allergic rhinitis therapeutics, cosmetic compositions, agrichemical compositions, insecticides, bactericides, herbicides, beverage or food compositions, and animal drug compositions.

Preferred specific examples of the extremely poorly water-soluble drug include antirheumatics such as 2-benzyl-5-(4-chlorophenyl)-6-[4-(methylthio)phenyl]-2H-pyridazin-3-one (may hereinafter be referred to as "Compound A"; solubility in water at 25° C.: 0.01 µg/mL), steroids such as prednisolone valerate acetate (solubility in water at 25° C.: 4.0 µg/mL), cholesterol (solubility in water at 25° C.: 0.1 µg/mL), estradiol (solubility in water at 25° C.: 3.6 µg/mL) and progesterone (solubility in water at 25° C.: 8.8 µg/mL), antiasthma drugs such as pranlukast (solubility in water at 25° C.: 0.9 µg/mL), and allergic rhinitis therapeutics such as pranlukast (solubility in water at 25° C.: 0.9 µg/mL). Compound A is particularly preferred.

The porous silica material for use in the present invention is a porous silica material (may hereinafter be referred to as "the instant porous silica material") which is characterized in that the porous silica material has an average pore diameter in a range of from 1 to 20 nm, pores having diameters within ±40% of the average pore size account for at least 60% of a total pore volume of the porous silica material, and in X-ray diffractometry, the porous silica material has at least one peak at a position of diffraction angle (2θ) corresponding to a d value of at least 1 nm.

The average pore diameter of the instant porous silica material can be determined by the gas adsorption method. Its measurement can be conducted, for example, by an automated specific surface area/pore distribution analyzer, "TRISTAR 3000" (manufactured by Micrometrics Instrument Corporation), or the like.

On the other hand, the expression that "in X-ray diffractometry of the instant porous silica material, it has at least one peak at a position of diffraction angle (2θ) corresponding to a d value of at least 1 nm" means that periodic structures of the d value corresponding to the peak angle exist in the porous silica material. This reflects a structure in which pores are arranged orderly at intervals of at least 1 nm. The instant porous silica material is, therefore, a porous silica material in which pore diameters are sufficiently uniform.

It is to be noted that X-ray diffractometry can be performed, for example, by an automated X-ray diffractometer system, "MXP 3" (manufactured by Mac Science Corporation), or the like.

The porous silica material for use in the present invention can have a composition consisting of pure silica. As an alternative, it can be a mixture of silica with one or more of aluminum (Al), titanium (Ti), magnesium (Mg), zirconium (Zr), gallium (Ga), beryllium (Be), yttrium (Y), lanthanum (La), tin (Sn), lead (Pb), vanadium (V), boron (B) and the like.

Examples of the porous silica material for use in the present invention include porous silica materials each having a skeleton of a polymerized metal oxide, typically porous silica materials each having a silicate skeleton. In the instant porous silica material, such metal-oxygen bonds are formed in a network structure, and as a whole, make up a porous material. Also included as examples are porous silica materials each of which has a skeleton containing, in place of a fraction of the silicon atoms in the silicate skeleton, other metal atoms such as aluminum, zirconium, tantalum, niobium, tin, hafnium, magnesium, molybdenum, cobalt, nickel, gallium, beryllium, yttrium, lanthanum, lead and/or vanadium atoms. Also usable are porous silica materials each of which has a skeleton containing such other metal atoms or silicon atoms in a silicate skeleton or a skeleton containing bonds of such other metal atoms and oxygen atoms.

It is to be noted that various metal atoms, organic functional groups and/or inorganic functional groups may be added to or as side chains bonded to atoms making up such a basic skeleton. Those containing, for example, thiol groups, carboxyl groups, lower alkyl groups such as methyl groups or ethyl groups, phenyl groups, amino groups, vinyl groups and or the like are preferred.

As the shape of pores in the porous silica material for use in the present invention, pores one-dimensionally extending in the form of a tunnel, box-shaped or ball-shaped pores three-dimensionally connected together, and the like can be mentioned. Examples of the pore structure of the porous silica material for use in the present invention include, but are not limited to, two-dimensional hexagonal structures, three-dimensional hexagonal structures (P6mm, P63/mmc), cubic structures (Ia3d, Pm3n), lamellar structures, disordered structures, and the like. Examples of the porous silica material for use in the present invention, therefore, include porous silica materials of various structures.

Commercial examples of such porous silica materials include "FSM-C8", "FSM-C10", "FSM-C12", "FSM-C14", "FSM-C16", "FSM-C18" and "FSM-C22" (all, products of Toyota Central R&D Labs. Inc.), and "MCM-41" (mesoporous molecular sieve, product of Mobil Chemical Corp.), with "FSM-C16" and "FSM-C12" being particularly preferred.

The porous silica material for use in the present invention can be produced by condensing a skeleton raw material in the presence of a surfactant and then removing the surfactant from the condensation product. More specifically, it is produced by condensing a skeleton raw material, such as sodium silicate, silica or an alkoxysilane, in a solution of a surfactant [production process (1)]. As an alternative, it is also produced by condensing a layer silicate (kanemite or the like) as a skeleton raw material in a solution of a surfactant [production process (2)]. A description will hereinafter be made about the production processes (1) and (2) both of which are preferred for obtaining the porous silica material for use in the present invention.

Production Process (1)

The instant porous silica material is produced by subjecting a skeleton raw material to a condensation reaction in a solvent with a surfactant dissolved therein, collecting the resulting precipitate or the resulting gel-form solid product by filtration, washing and drying the precipitate or solid product, and then subjecting the precipitate or solid product to calcination treatment or $H^+$ substitution treatment to remove the surfactant.

Examples of the skeleton raw material include tetraalkoxysilanes and alkylalkoxysilanes containing three or four $C_{1-4}$ alkoxy groups, preferably tetraalkoxysilanes having four $C_{1-3}$ alkoxy groups, especially preferably tetraethoxysilane and tetramethoxysilane. These alkoxysilanes can be used either singly or in combination.

As the solvent, water or a mixed solvent of water and an organic solvent miscible with water is preferred. Examples of the organic solvent include alcohols such as methanol, ethanol, propanol, ethylene glycol and glycerin, acetone, pyridine, acetonitrile, tetrahydrofuran, dioxane, dimethylformamide, N-methylpyrrolidone, dimethylacetamide, and dimethylsulfoxide, with methanol being particularly preferred.

No particular limitation is imposed on the surfactant. In general, a cationic, anionic or nonionic surfactant can be used. Preferred examples include cationic surfactants such as the chlorides, bromides, iodides and hydroxides of alkyltrimethylammonium ($C_nH_{2n+1}N^+(CH_3)_3$; n being an integer of from 2 to 18), alkylammonium, dialkyldimethylammonium and benzylammonium, with the hydroxides and bromides of hexadecyltrimethylammonium and dodecyltrimethylammonium being particularly preferred.

The concentration of the surfactant may preferably be from 0.05 to 0.5 mol/L, although no particular limitation is imposed thereon. A concentration lower than 0.05 mol/L results in incomplete formation of pores, while a concentration higher than 0.5 mol/L leads to an impairment in the uniformity of pore diameters.

The pH control of the reaction solvent can be effected with an alkali such as sodium hydroxide or an acid such as hydrochloric acid subsequent to addition of a cationic surfactant. When water is used as the solvent, it is preferred to conduct the reaction at pH 10 or higher and then to neutralize the reaction mixture with an acid to pH 9 or lower (more preferably 8 or lower). When a mixed water/alcohol solvent is used, on the other hand, it is not specifically required to neutralize the reaction mixture with an acid subsequent to conducting the reaction at pH 10 or higher. By conducting the reaction as is without acid neutralization, the condensation can proceed.

The temperature during the reaction may preferably in a range of from −50 to 100° C. Especially when the solvent is water, a range of from 60 to 80° C. is preferred. When the solvent is a mixed water/methanol solvent, the reaction can be conducted at room temperature.

The reaction can be conducted for 1 to 48 hours or even longer, although the reaction time can differ as needed depending on the reaction solvent. When the solvent is water, for example, it is preferred to conduct the reaction for 1 hour or longer at pH 10 or higher, or for 3 hours or longer at pH 9 or lower (more preferably, pH 8 or lower). Under each of these pHs, the reaction is preferably conducted under stirring.

The instant porous silica material can be obtained by collecting, subsequent to a condensation reaction, the resulting precipitate or the resulting gel-form solid product by filtration, washing and drying the precipitate or solid product, and then subjecting the precipitate or solid product to calcination treatment or $H^+$ substitution treatment to remove the surfactant.

According to the process relying upon conducting calcination treatment, the solid reaction product is heated at 300 to 1,000° C. (preferably 400 to 700° C.). The heating time can preferably be 30 minutes or longer. For the complete removal of organic substances, it is particularly preferred to heat the solid reaction product for 1 hour or longer. As described in the above, it is preferred to conduct the calcination treatment in an inert gas (nitrogen or the like) atmosphere until up to about 400° C. to avoid burning.

According to the process relying upon conducting $H^+$ substitution treatment with an alcohol or the like, the solid reaction product is dispersed in a solution consisting of a solvent having high solubility for the surfactant and a small amount of an ion source of the same charge as the surfactant added therein. After stirring the dispersion, the resulting solid component is recovered. Examples of the solvent include ethanol, methanol, and acetone, with ethanol being particularly preferred.

It is to be noted that this production process can also produce a porous silica material formed of a basic skeleton including an element (for example, a metal element) other than silicon. Typically, the production can be realized by adding, as raw materials for forming the basic skeleton, sodium silicate, silica or an alkoxysilane together with a compound containing an element other than silicon and then conducting the above-described condensation reaction.

Production Process (2)

The instant porous silica material is produced by subjecting a layer material such as a layer silicate as a skeleton raw material to a condensation reaction in a solvent with a surfactant dissolved therein, collecting the resulting solid product by filtration, washing and drying the solid product, and then subjecting the solid product to calcination treatment or $H^+$ substitution treatment to remove the surfactant.

As the layer silicate for use as the skeleton raw material, it is possible to use at least one or more silicates selected from the group consisting of kanemite ($NaHSi_2O_3 \cdot 3H_2O$), sodium disilicate crystals ($\alpha$-, $\beta,\gamma,\delta$-$Na_2Si_2O_3$), makatite ($Na_2Si_4O_9 \cdot 5H_2O$), ilerite ($Na_2Si_8O_{17} \cdot XH_2O$), magadiite ($Na_2Si_{14}O_{29} \cdot XH_2O$), kenyaite ($Na_2Si_{20}O_{41} \cdot XH_2O$) and the like.

Other usable layer silicates include, for example, those obtained by treating clay minerals, such as sepiolite, montmorillonite, vermiculite, mica, kaolinite and smectite with an acidic aqueous solution to remove elements other than silica.

It is also possible to use one or more silicates other than layer silicates, which are selected from the group consisting of water glass, glass, amorphous sodium silicate, silicon alkoxides (tetraethyl orthosilicate and the like), and the like.

No particular limitation is imposed on the surfactant. In general, a variety of surfactants which are cationic, anionic or nonionic can be mentioned. Preferred examples include cationic surfactants such as the chlorides, bromides, iodides and hydroxides of alkyltrimethylammonium ($C_nH_{2n+1}N^+(CH_3)_3$; n being an integer of from 2 to 18), alkylammonium, dialkyldimethylammonium and benzylammonium. In addition, fatty acid salts, alkylsulfonate salts, alkylphosphate salts, polyethylene-oxide-based ionic surfactants, and the like are also usable. It is to be noted that as the surfactant, these exemplified surfactants can be used either singly or in combination.

The layer silicate and the surfactant are mixed together under acidic or alkaline conditions, and as a result, the layer silicate is partially condensed.

The concentration of the surfactant may preferably be from 0.05 to 0.5 mol/L, although no particular limitation is imposed thereon. A concentration lower than 0.05 mol/L results in incomplete formation of pores, while a concentration higher than 0.5 mol/L leads to an impairment in the uniformity of pore diameters.

The solvent which makes up the reaction system can preferably be water. As an alternative, a mixed solvent with a water-miscible organic solvent such as an alcohol mixed therein is also usable.

Examples of the organic solvent include alcohols such as methanol, ethanol, propanol, ethylene glycol and glycerin, acetone, pyridine, acetonitrile, tetrahydrofuran, dioxane, dimethylformamide, N-methylpyrrolidone, dimethylacetamide, and dimethylsulfoxide, with methanol being particularly preferred.

The condensation reaction can be conducted preferably under the conditions that the solution with the layer silicate dispersed therein is heated at 30 to 100° C. (more preferably at 60 to 80° C., still more preferably at 70 to 80° C.), and the reaction time can be set preferably for 2 to 24 hours. It is also preferred to stir the dispersion during the reaction under heating.

The pH of the dispersion may be controlled preferably at 10 or higher during an initial stage (typically, the first 1 to 5 hours) of the condensation reaction, and subsequently (typically, after an elapse for 1 hour or longer), at 10 or lower.

The pH control can be effected with an alkali such as sodium hydroxide or an acid such as hydrochloric acid. By such pH control, a porous silica material excellent in crystallinity and heat resistance can be obtained. It is to be noted that, as kanemite is alkaline, the pH of its dispersion can generally be 10 or higher without any particular adjustment when the solvent is water.

By conducting such a dehydrating condensation reaction, a structure (porous silica precursor) is obtained with pores formed using the employed surfactant as templates. Accordingly, subsequent to the completion of the condensation reaction, the resulting solid reaction product (porous silica precursor) is collected by filtration from the dispersion. It is preferred to repeatedly wash the thus-obtained solid reaction product with water at this stage. It is desired to dry the solid reaction product after the washing.

By subsequently subjecting the solid reaction product to calcination treatment preferably at a temperature at 550° C. or higher or to $H^+$ substitution treatment with a hydrochloric acid/ethanol solution, the surfactant held as the templates within the pores of the precursor can be removed. When a cationic surfactant is used, for example, the solid reaction product is dispersed in ethanol with a small amount of hydrochloric acid added therein, and stirring is then conducted with heating at 50 to 70° C. In the case of an anionic surfactant, the surfactant can be extracted in a solvent with anions added therein. In the case of a nonionic surfactant, on the other hand, the surfactant can be extracted with a solvent only. When the above-described calcination treatment is conducted, it is preferred to conduct the calcination treatment in an inert gas (nitrogen or the like) atmosphere to avoid burning. Even in this case, however, it is preferred, from the viewpoint of preventing carbon and the like from remaining, to convert the atmosphere into an oxidizing atmosphere such as air in a final stage of the calcination treatment.

By the above-mentioned treatment step, the templates are removed to leave pores behind so that the desired porous silica material is produced.

In the process for producing a porous silica material by using a layer material, the use of a layer material having a basic skeleton containing an element other than silicon makes it possible to produce a porous material having such a basic skeleton. As a method for adding an element other than silicon into the above-described porous material, the following methods can be mentioned: (1) to incorporate the element other than silica in a layer silicate as a raw material, (in other words, to use a layer silicate containing the element other than silicon), and (2) to add a substance, which contains the element other than silicon, in the course of the synthesis of the porous silica material. To incorporate an element other than silicon (for example, aluminum) as described above, aluminum nitrate, sodium aluminate or the like can be used.

The average pore diameter of the porous silica material for use in the present invention can be preferably from 1 to 20 nm, more preferably from 1.5 to 10 nm, especially preferably from 2 to 3 nm.

The specific surface area of the porous silica material for use in the present invention can be preferably from 100 to 2,000 $m^2/g$, more preferably from 600 to 1,800 $m^2/g$, especially preferably from 800 to 1,500 $m^2/g$. It is to be noted that the specific surface area can be measured by the adsorption method.

The mixing weight ratio of the porous silica material to the very slight water-soluble drug to be used in the present invention can be preferably from 0.1:1 to 1,000:1, more preferably from 0.5:1 to 100:1, especially preferably from 1:1 to 50:1.

Examples of carbon dioxide for use in the present invention include liquid carbon dioxide, gaseous carbon dioxide, and dry ice.

The term "supercritical state" as used herein means a state in which the pressure and the temperature both exceed the critical points (in the case of carbon dioxide, pressure: about 7.38 MPa, temperature: about 31.0° C.), while the term "subcritical state" as used herein means a state in which only one of the pressure and the temperature exceeds the corresponding critical point. The term "critical points" has a meaning, for example, as described in detail by J. W. Tom and P. G. Debenedetti in FIG. 1 of "Particle Formation with Supertirical Fluids—A Review", J. Aerosol Sci., 22(5), 555-584 (1991).

The weight ratio of the extremely poorly water-soluble drug to the supercritical fluid or subcritical fluid of carbon dioxide in the present invention can be preferably from 1:1 to 1:1,000,000, more preferably from 1:10 to 1:100,000, especially preferably from 1:50 to 1:50,000.

The time of the treatment with the supercritical fluid or subcritical fluid of carbon dioxide in the present invention can be preferably from 1 minute to 24 hours, more preferably from 0.5 to 12 hours, especially preferably from 1 to 8 hours.

The treatment with the supercritical fluid or subcritical fluid of carbon dioxide in the present invention can be conducted in a pressure vessel, a supercritical extraction system, a supercritical micronization system, another testing system for supercritical fluid or subcritical fluid, or the like. Illustrative are "PORTABLE REACTOR" (manufactured by Taiatsu Techno Corporation), "SUPERCRITICAL EXTRACTION SYSTEM SCF-GET" (manufactured by JASCO Corporation), and "SUPERCRITRICAL MICRONIZATION SYSTEM SC SPRAYER" (manufactured by Nikkiso Co., Ltd.). These treatment vessels can each have a construction equipped with a stirring mechanism to stir the supercritical fluid or subcritical fluid.

The temperature of the treatment with the supercritical fluid or subcritical fluid in the present invention can be preferably from −40 to 100° C., more preferably from 0 to 80° C., especially preferably from 10 to 60° C., although it differs depending on the kind of the extremely poorly water-soluble drug.

The pressure of the treatment with the supercritical fluid or subcritical fluid in the present invention can be preferably from 1 to 50 MPa, more preferably from 1 to 40 MPa, especially preferably from 6 to 30 MPa, although it differs depending on the kind of the extremely poorly water-soluble drug.

No particular limitation is imposed on the production step of treating with the supercritical fluid or subcritical fluid of carbon dioxide in the present invention. For example, the following production processes can be mentioned: (1) placing the instant porous silica material and the very slight water-soluble drug in a pressure vessel, filling the pressure vessel with carbon dioxide, treating the porous silica material and the extremely poorly water-soluble drug while controlling a temperature and pressure within the vessel such that carbon dioxide is maintained in a supercritical state or subcritical state, and then discharging carbon dioxide to recover the resulting composition, (2) placing the instant porous silica material and the extremely poorly water-soluble drug in a pressure vessel, controlling a temperature within the vessel such that carbon dioxide will be maintained in a supercritical state or subcritical state, filling the pressure vessel with carbon dioxide at such a pressure that carbon dioxide is maintained in the supercritical state or subcritical state, maintaining the supercritical state or subcritical state to treat the porous silica material and the extremely poorly water-soluble drug, and then discharging carbon dioxide to recover the resulting composition.

In general, the composition according to the present invention obtained as described above, said composition containing the extremely poorly water-soluble drug, can have a weight average particle size preferably of from 1 μm or greater, more preferably of from 1 to 2,000 μm, particularly preferably of from 3 to 500 μm. It is to be noted that the weight average particle size can be measured by laser diffractometry, and the like.

Upon treating the porous silica material and the extremely poorly water-soluble drug with the supercritical fluid or subcritical fluid of carbon dioxide in the present invention, various components authorized as drug additives can be added as desired insofar as they do not impair the advantageous effects of the present invention. Such components can include, for example, solvents, polymer compounds, and surfactants.

Examples of the solvents include water; aromatic hydrocarbons such as benzene, toluene and xylene; ethers such as dimethyl ether, diethyl ether, dioxane, diethoxyethane, tetrahydrofuran and 1,2-dimethoxyethane; chlorinated organic solvents such as dichloromethane, chloroform, carbon tetrachloride and 1,2-dichloroethane; alkylnitriles such as acetonitrile and propionitrile; nitroalkanes such as nitromethane and nitroethane; amides such as N,N-dimethylformamide and N,N-dimethylacetamide; ketones such as acetone; fatty acids such as acetic acid and oleic acid; alcohols such as methanol, ethanol and isopropanol; sulfoxides such as dimethylsulfoxide; and mixed solvents thereof.

Examples of the polymer compounds include pullulan, sodium carboxymethylcellulose, sodium alginate, xanthan gum, polyvinylpyrrolidone, carboxyvinyl polymer, methylcellulose, hydroxypropylmethylcellulose, carageenan, agar, and gelatin.

Examples of the surfactants include nonionic surfactants, for example, polyoxyethylene polyoxypropylene glycol, polyoxyethylene hydrogenated castor oil, polyoxyethylene alkyl ethers such as polyoxyethylene lauryl ether, and sorbitan fatty acid esters such as polyoxyethylene sorbitan fatty acid ester (polysolvate) and sorbitan monostearate; cationic surfactants such as benzalconium chloride, benzethonium chloride and cetylpyridinium chloride; and anionic surfactants such as calcium stearate, magnesium stearate and sodium laurylsulfate. Also included are fluorine-containing surfactants such as ammonium carboxylate perfluoroether.

One or more of additives commonly employed in medicinal preparations can be added to the composition according to the present invention, which contains the extremely poorly water-soluble drug, to produce an oral preparation or parenteral preparation, although as a medicinal preparation, the composition can be used as is.

Exemplified as additives for oral preparations are excipients such as lactose, crystalline cellulose, sucrose, mannitol, light silicic anhydride, and calcium hydrogenphosphate; binders such as methylcellulose, hydroxypropylcellulose, hydroxypropylmethylcellulose, gelatin, polyvinylpyrrolidone, and pullulan; disintegrators such as crosslinked sodium carboxymethylcellulose, sodium carboxymethylcellulose, crosslinked polyvinylpyrrolidone, and low-substituted hydroxypropylcellulose; lubricants such as magnesium stearate and talc; colorants such as tar colors and iron sesquioxide; and corrigents such as stevia, aspartame, and flavors.

Exemplified as additives for parenteral preparations are solvents, for example, monohydric alcohol such as benzyl alcohol, polyhydric alcohols such as concentrated glycerin and 1,3-butylene glycol, esters such as diisopropyl adipate and triacetine, ketones such as crotamiton, and oils and fats such as oleic acid and castor oil; water-soluble polymer substances, for example, celluloses such as hydroxyethyl cellulose and hydroxypropylcellulose, polysaccharides such as sucrose and β-cyclodextrin; sugar alcohols such as sorbitol and mannitol, and synthetic polymer substances such as polyvinyl alcohol, polyvinylpyrrolidone and polyacrylic acid; surfactants, for example, anionic surfactants such as calcium stearate, magnesium stearate and sodium laurylsulfate, cationic surfactants such as benzalconium chloride, benzethonium chloride and cetylpyridium chloride, and nonionic surfactants such as glycerin monostearate, sugar fatty acid esters, polyoxyethylene hydrogenated castor oil and polyoxyethylene sorbitan fatty acid esters; enhancers, for example, esters such as isopropylmyristate, terpenes such as L-menthol and dL-camphor, and higher fatty acids such as oleic acid; stabilizers, for example, phenolic substances such as methyl paraoxybenzoate and propyl paraoxybenzoate, neutral substances such as chlorobutanol and phenylethyl alcohol, cationic soaps such as benzalconium chloride and benzethonium chloride, antioxidants such as vitamin E and buthylhydroxyanisole, reducing agents such as ascorbic acid, sodium hydrogensulfite and sodium thiosulfate, and chelating agents such as citric acid and tartaric acid and salts thereof, lecithin, ethylenediamine tetraacetate (edetic acid); pH adjustors such as phosphoric acid, acetic acid, boric acid, succinic acid, phthalic acid and salts thereof, glycine, and sodium hydroxide; and bases such as polyacrylic acid (sodium salt), polyvinylpyrrolidone, polyvinyl alcohol, carboxyvinyl polymer, gelatin, and starch.

Exemplified as the forms of preparations according to the present invention are oral preparations such as tablets, capsules, granules and subtilized granules; and parenteral preparations such as injections, suppositories, vaginal preparations, sublingual preparations, implants, instillations and sprays.

EXAMPLES

The present invention will be described more specifically on the basis of examples and comparative examples, although the present invention shall not be limited to or by the following examples.

Example 1

Compound A (30 mg), "FSM-C16" (product of Toyota Central R&D Labs. Inc.; 300 mg) and dry ice (120 g) were placed in a "PORTABLE REACTOR" (manufactured by Taiatsu Techno Corporation), and were heated to 50° C. to raise the pressure to 18 MPa. At those temperature and pressure, the contents were maintained under stirring for 5 hours. Subsequently, the heating was stopped, and the reaction mixture was allowed to stand until its temperature dropped to room temperature. After carbon dioxide was discharged, a composition with the extremely poorly water-soluble drug contained therein was obtained.

Example 2

Compound A (30 mg), "FSM-C12" (product of Toyota Central R&D Labs. Inc.; 300 mg) and dry ice (120 g) were placed in a "PORTABLE REACTOR", and were heated to 50° C. to raise the pressure to 18 MPa. At those temperature and pressure, the contents were maintained under stirring for 5 hours. Subsequently, the heating was stopped, and the reaction mixture was allowed to stand until its temperature dropped to room temperature. After carbon dioxide was discharged, a composition with the extremely poorly water-soluble drug contained therein was obtained.

Comparative Example 1

Compound A (30 mg) and "FSM-C16" (300 mg) were mixed in a mortar to obtain a composition with the extremely poorly water-soluble drug contained therein.

Comparative Example 2

Compound A (30 mg) and dry ice (120 g) were placed in a "PORTABLE REACTOR", and were heated to 50° C. to raise the pressure to 18 MPa. At those temperature and pressure, the contents were maintained under stirring for 5 hours. Subsequently, the heating was stopped, and the reaction mixture was allowed to stand until its temperature dropped to room temperature. After carbon dioxide was discharged, a composition with the extremely poorly water-soluble drug contained therein was obtained.

Dissolution Test

With respect to the compositions containing the extremely poorly water-soluble drug and obtained in Examples 1-2 and Comparative Examples 1-2, a dissolution test was conducted. The dissolution test was conducted in accordance with The Pharmacopoeia of Japan, General Tests, Dissolution Test, Method 2 (paddle method). Each composition with the extremely poorly water-soluble drug (Compound A, 5 mg) contained therein was added to a test solution (0.3% aqueous solution of sodium laurylsulfate; 900 mL), and a dissolution test was conducted under the following conditions: temperature: 37±1° C., paddle rotation speed: 50 rpm).

After 5, 30, 60 and 120 minutes, Compound A dissolved in the test solution was quantified by liquid chromatography while using a reversed phase column ("INERTSIL ODS-2", product of GL Sciences Inc.), and dissolution rates (%) were calculated.

The results of the measurement are shown in Table 1.

TABLE 1

|  |  | Example | | Comparative Example | |
|---|---|---|---|---|---|
|  |  | 1 | 2 | 1 | 2 |
| Compound A (mg) | | 30 | 30 | 30 | 30 |
| "FSM-C16" (mg) | | 300 | — | 300 | — |
| "FSM-C12" (mg) | | — | 300 | — | — |
| Dry ice (g) | | 120 | 120 | — | 120 |
| Average pore diameter (nm) | | 3 | 2 | 3 | — |
| Dissolution rate (%) | Stirring time (min) | | | | |
|  | 5 | 29.5 | 22.0 | 3.9 | 0.0 |
|  | 30 | 54.8 | 40.7 | 7.6 | 1.7 |
|  | 60 | 63.9 | 51.2 | 10.0 | 1.1 |
|  | 120 | 74.7 | 57.2 | 14.3 | 2.2 |

From the composition containing the extremely poorly water soluble drug obtained by simply physically mixing Compound A and the porous silica material (Comparative Example 1) and the composition containing the extremely poorly water soluble drug obtained by conducting treatment of Compound A with supercritical carbon dioxide without inclusion of the porous silica material (Comparative Example 2), Compound A was not dissolved practically. On the other hand, the compositions containing the extremely poorly water soluble drug according to the present invention, which were obtained by adding Compound A and the porous silica material and treating them with supercritical carbon dioxide (Examples 1-2), both exhibited dramatic improvements in the dissolution of Compound A.

Production Example 1

The composition (150 g) of Example 1, which contained the extremely poorly water-soluble drug, was classified by a "NEW SPEED MILL ND-02" (manufactured by Okada Seiko Co., Ltd.) equipped with a screen having an opening size of 1 mm in diameter. The thus-classified composition with the extremely poorly water-soluble drug contained therein (110 g), lactose (100 mesh lactose, product of DMV NV, 42 g), crystalline cellulose ("AVICEL PH-102", product of Asahi Kasei Corporation, 100 g) and low-substituted hydroxypropylcellulose ["L-HPC(LH-11)", product of Shin-Etsu Chemical Co., Ltd., 45 g] were mixed for 10 minutes by a V-blender. Magnesium stearate (3 g) was added to the mixture, followed by further mixing for 5 minutes in the twin-cylinder mixer. The resulting mixture was compressed into tables on a tablet machine ("AP-38", manufactured by Hata Iron Works Co., Ltd.) to produce tables of 300 mg/table (each contained 100 mg of Compound A).

The invention claimed is:
1. A composition, comprising:
an extremely poorly water-soluble drug; and
a porous silica material;
wherein:
the composition is obtained by treating a mixture comprising the porous silica material and the extremely poorly water-soluble drug with a supercritical fluid or subcritical fluid of carbon dioxide;
the extremely poorly water-soluble drug has a solubility in water at 25° C. of less than 10 μg/mL prior to treatment;
the porous silica material has an average pore diameter of from 1 to 20 nm, a total pore volume of pores having diameters within ±40% of the average pore diameter accounts for at least 60% of a volume of all pores of the porous silica material, and the porous silica material has an X-ray diffraction pattern including at least one peak at a position of a diffraction angle (2θ) corresponding to a d value of at least 1 nm; and
the composition is suitable for oral administration.

2. The composition according to claim 1, wherein the porous silica material has a specific surface area of from 100 to 2,000 m$^2$/g.

3. The composition according to claim 1, wherein a mixing ratio the porous silica material to the extremely poorly water-soluble drug is from 0.1:1 to 1,000:1.

4. The composition according to claim 1, wherein the extremely poorly water-soluble drug comprises 2-benzyl-5-(4-chlorophenyl)-6-[4-(methylthio)phenyl]-2H-pyridazin-3-one.

5. A medicinal preparation comprising:
the composition according to claim 1; and
an additive.

6. A process for producing the composition according to claim 1, comprising:
placing a porous silica material and an extremely poorly water-soluble drug in a pressure-resistant vessel;
filling the pressure-resistant vessel with carbon dioxide;
maintaining the vessel at a temperature and pressure such that the carbon dioxide is maintained as a supercritical fluid or a subcritical fluid; and
discharging the carbon dioxide to recover the resulting composition;
wherein the porous silica material has an average pore diameter of from 1 to 20 nm, a total pore volume of pores having diameters within ±40% of the average pore diameter accounts for at least 60% of a volume of all pores of the porous silica material, and the porous silica material has an X-ray diffraction pattern including at least one peak at a position of a diffraction angle (2θ) corresponding to a d value of at least 1 nm.

7. The process of claim 6, wherein a weight ratio of the extremely poorly water-soluble drug to the supercritical fluid or subcritical fluid of carbon dioxide is from 1:1 to 1:1,000,000.

8. The process of claim 6, wherein maintaining the vessel comprises maintaining the vessel at a temperature of from −40 to 100° C.

9. The process of claim 6, wherein maintaining the vessel comprises maintaining the vessel at a pressure of from 1 to 50 MPa.

10. The process of claim 6, wherein the porous silica material and the extremely poorly water-soluble drug are maintained in contact with the supercritical fluid or subcritical fluid of carbon dioxide for a period of from 1 minute to 24 hours.

11. A process for producing a composition according to claim 1, comprising:
   placing a porous silica material and an extremely poorly water-soluble drug in a pressure-resistant vessel;
   maintaining the vessel at a temperature at which carbon dioxide is in the form of a supercritical fluid or a subcritical fluid;
   filling the vessel with carbon dioxide at a pressure such that carbon dioxide is in the form of a supercritical fluid or a subcritical fluid;
   treating the porous silica material and the extremely poorly water-soluble drug with the supercritical fluid or subcritical fluid of carbon dioxide; and
   discharging carbon dioxide to recover the resulting composition;
   wherein the porous silica material has an average pore diameter of from 1 to 20 nm, a total pore volume of pores having diameters within ±40% of the average pore diameter accounts for at least 60% of a volume of all pores of the porous silica material, and the porous silica material has an X-ray diffraction pattern including at least one peak at a position of a diffraction angle (2θ) corresponding to a d value of at least 1 nm.

12. The process according to claim 11, wherein a weight ratio of the extremely poorly water-soluble drug to the supercritical fluid or subcritical fluid of carbon dioxide is from 1:1 to 1:1,000,000.

13. The process according to claim 11, wherein treating the porous silica material and the extremely poorly water-soluble drug comprises treating at a temperature of from −40 to 100° C.

14. The process according to claim 11, wherein treating the porous silica material and the extremely poorly water-soluble drug comprises treating at a pressure of from 1 to 50 MPa.

15. The process according to claim 11, wherein treating the porous silica material and the extremely poorly water-soluble drug comprises treating for a period of from 1 minute to 24 hours.

* * * * *